(12) United States Patent
Smith

(10) Patent No.: US 9,078,699 B2
(45) Date of Patent: *Jul. 14, 2015

(54) TROCAR ASSEMBLY WITH ROTATABLE OBTURATOR HOUSING

(75) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 985 days.

This patent is subject to a terminal disclaimer.

(21) Appl. No.: 13/165,217

(22) Filed: Jun. 21, 2011

(65) Prior Publication Data

US 2011/0251633 A1    Oct. 13, 2011

Related U.S. Application Data

(63) Continuation of application No. 11/171,052, filed on Jun. 30, 2005, now Pat. No. 7,988,670.

(51) Int. Cl.
*A61B 17/00* (2006.01)
*A61B 17/34* (2006.01)

(52) U.S. Cl.
CPC ......... *A61B 17/3496* (2013.01); *A61B 17/3474* (2013.01)

(58) Field of Classification Search
CPC ........... A61B 17/3496; A61B 17/3474; A61B 17/34; A61B 17/3494
USPC ........................................................ 604/232
See application file for complete search history.

(56) References Cited

U.S. PATENT DOCUMENTS

| | | | |
|---|---|---|---|
| 3,713,447 A | 1/1973 | Adair | |
| 3,788,320 A | 1/1974 | Dye | |

(Continued)

FOREIGN PATENT DOCUMENTS

| | | |
|---|---|---|
| EP | 0617924 A2 | 10/1994 |
| EP | 0769278 A2 | 4/1997 |

(Continued)

OTHER PUBLICATIONS

European Search Report for corresponding EP Application No. EP 06013243 date of completion Nov. 16, 2006 (3 pages).

(Continued)

*Primary Examiner* — Aarti B Berdichevsky

(57) ABSTRACT

A trocar system includes a cannula having a cannula housing and a cannula sleeve extending from the cannula housing, and an obturator at least partially positionable within the cannula. The obturator includes an obturator housing adapted for mating with the cannula housing, an obturator shaft connected to the obturator housing and receivable within the cannula sleeve, an obturator blade connected to the obturator shaft, a protective member including a protective guard coaxially mounted about the obturator blade and a latch member associated with the obturator housing and operatively connected to the protective guard. The obturator shaft and the obturator blade are adapted for relative rotational movement. The protective guard is adapted for longitudinal movement between a first position substantially enclosing the obturator blade and a second position to at least partially expose the obturator blade. The latch member is moveable from an initial position securing the protective guard in the first position to an actuated position operatively releasing the protective guard to permit the protective guard to move to the second position thereof. The latch member is preferably adapted to move to the actuated position upon mating of the obturator housing and the cannula housing.

20 Claims, 10 Drawing Sheets

(56) References Cited

U.S. PATENT DOCUMENTS

| | | |
|---|---|---|
| 4,384,943 A | 5/1983 | Stoner et al. |
| 4,535,773 A | 8/1985 | Yoon |
| 4,654,030 A | 3/1987 | Moll et al. |
| 4,931,042 A | 6/1990 | Holmes et al. |
| 5,066,288 A | 11/1991 | Deniega et al. |
| 5,104,382 A | 4/1992 | Brinkerhoff et al. |
| 5,114,407 A | 5/1992 | Burbank |
| 5,248,298 A | 9/1993 | Bedi et al. |
| 5,256,149 A | 10/1993 | Banik et al. |
| 5,267,965 A | 12/1993 | Deniega |
| 5,314,417 A | 5/1994 | Stephens et al. |
| 5,342,382 A | 8/1994 | Brinkerhoff et al. |
| 5,364,372 A | 11/1994 | Danks et al. |
| 5,372,588 A | 12/1994 | Farley et al. |
| 5,387,197 A | 2/1995 | Smith et al. |
| 5,399,167 A | 3/1995 | Deniega |
| 5,445,142 A | 8/1995 | Hassler, Jr. |
| 5,534,009 A | 7/1996 | Lander |
| 5,536,259 A | 7/1996 | Utterberg |
| 5,545,150 A | 8/1996 | Danks et al. |
| 5,554,137 A | 9/1996 | Young et al. |
| 5,569,292 A | 10/1996 | Scwemberger et al. |
| 5,575,780 A | 11/1996 | Saito |
| 5,591,186 A | 1/1997 | Wurster et al. |
| 5,607,440 A | 3/1997 | Danks et al. |
| 5,609,604 A | 3/1997 | Schwemberger et al. |
| 5,624,459 A | 4/1997 | Kortenbach et al. |
| 5,658,236 A | 8/1997 | Sauer et al. |
| 5,690,664 A | 11/1997 | Sauer et al. |
| 5,697,913 A | 12/1997 | Sierocuk et al. |
| 5,697,947 A | 12/1997 | Wolf et al. |
| 5,709,671 A | 1/1998 | Stephens et al. |
| 5,776,112 A | 7/1998 | Stephens et al. |
| 5,797,943 A | 8/1998 | Danks et al. |
| 5,810,863 A | 9/1998 | Wolf et al. |
| 5,860,996 A | 1/1999 | Urban et al. |
| 5,868,773 A | 2/1999 | Danks et al. |
| 5,904,699 A | 5/1999 | Schwemberger et al. |
| 5,906,595 A | 5/1999 | Powell et al. |
| 5,947,930 A | 9/1999 | Schwemberger et al. |
| 5,984,941 A | 11/1999 | Wilson et al. |
| 5,997,510 A | 12/1999 | Schwemberger |
| 6,017,356 A | 1/2000 | Frederick et al. |
| 6,063,099 A | 5/2000 | Danks et al. |
| 6,077,284 A | 6/2000 | Piraka |
| 6,213,989 B1 | 4/2001 | Utterberg |
| 6,270,501 B1 | 8/2001 | Freiberg et al. |
| 6,296,651 B1 | 10/2001 | Lary et al. |
| 6,319,266 B1 * | 11/2001 | Stellon et al. .................. 606/185 |
| 6,497,687 B1 | 12/2002 | Blanco |
| 6,685,630 B2 | 2/2004 | Sauer et al. |
| 6,716,201 B2 | 4/2004 | Blanco |
| 6,837,874 B1 | 1/2005 | Popov |
| 7,988,670 B2 * | 8/2011 | Smith ....................... 604/165.04 |
| 2002/0143236 A1 | 10/2002 | Sauer et al. |
| 2003/0004529 A1 | 1/2003 | Tsonton et al. |
| 2004/0167557 A1 | 8/2004 | Kieturakis et al. |

FOREIGN PATENT DOCUMENTS

| | | |
|---|---|---|
| WO | 0121231 | 3/2001 |
| WO | 2007035889 | 3/2007 |

OTHER PUBLICATIONS

European Search Report, Application No. EP 08251780 dated Dec. 9, 2008.

European Search Report, Application No. EP 08251780 dated Aug. 28, 2008.

* cited by examiner

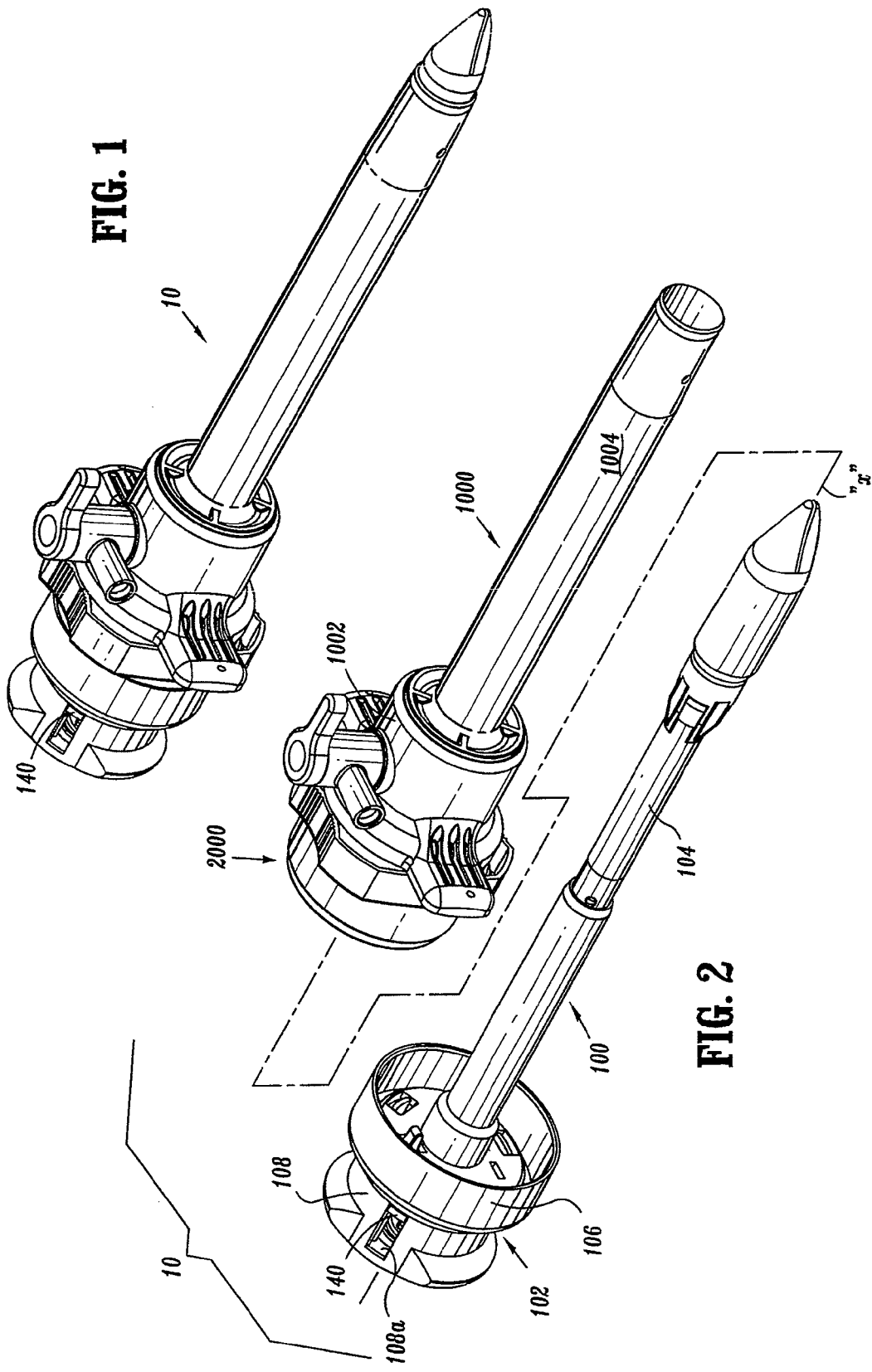

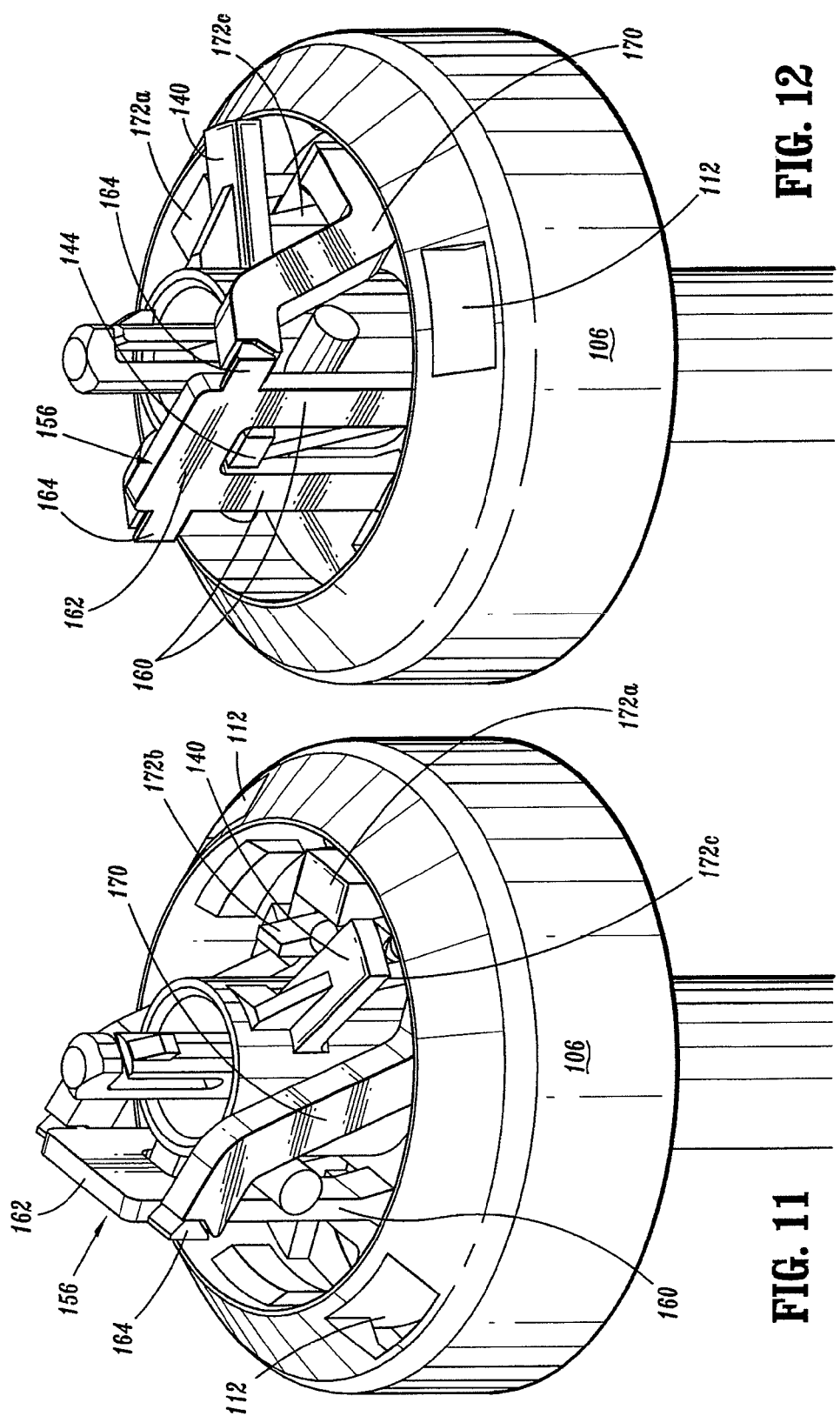

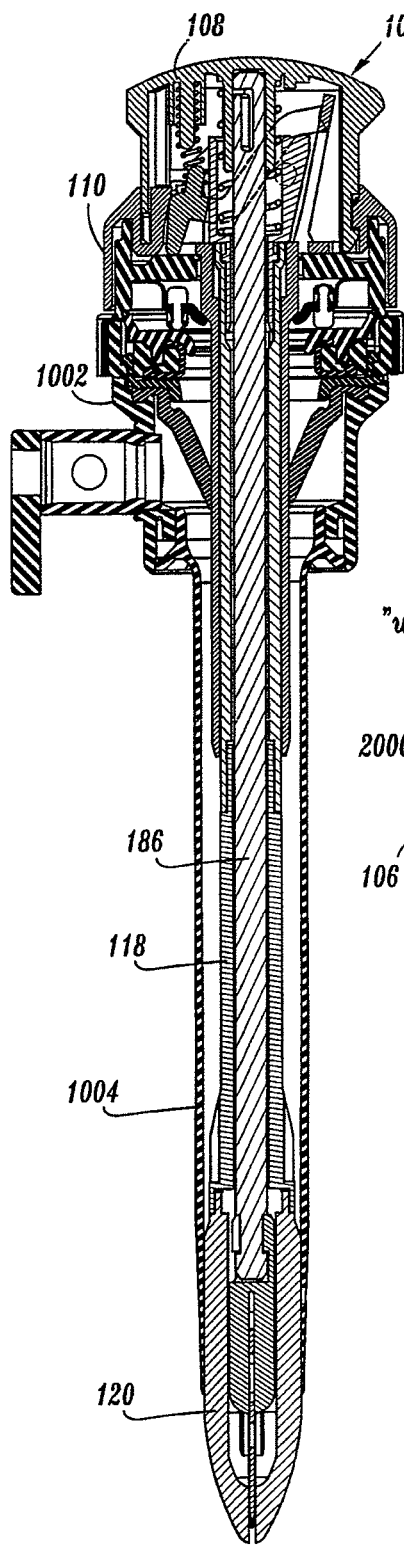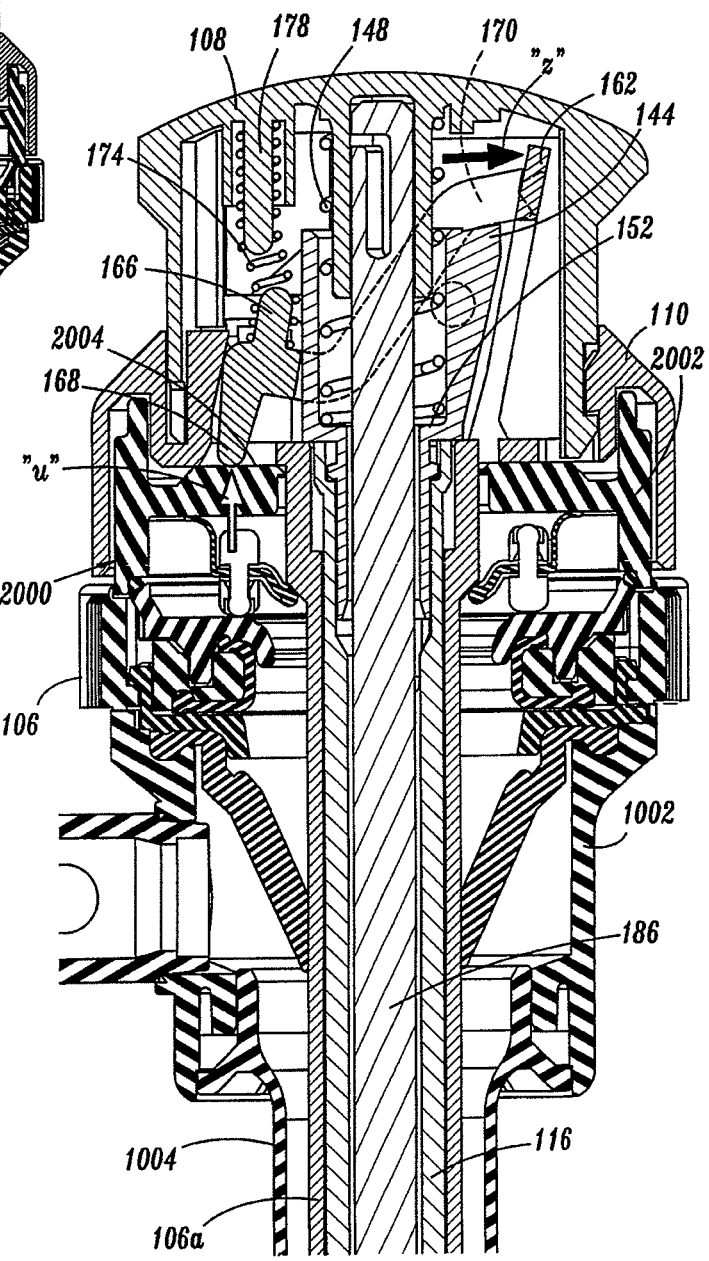
FIG. 14
FIG. 15

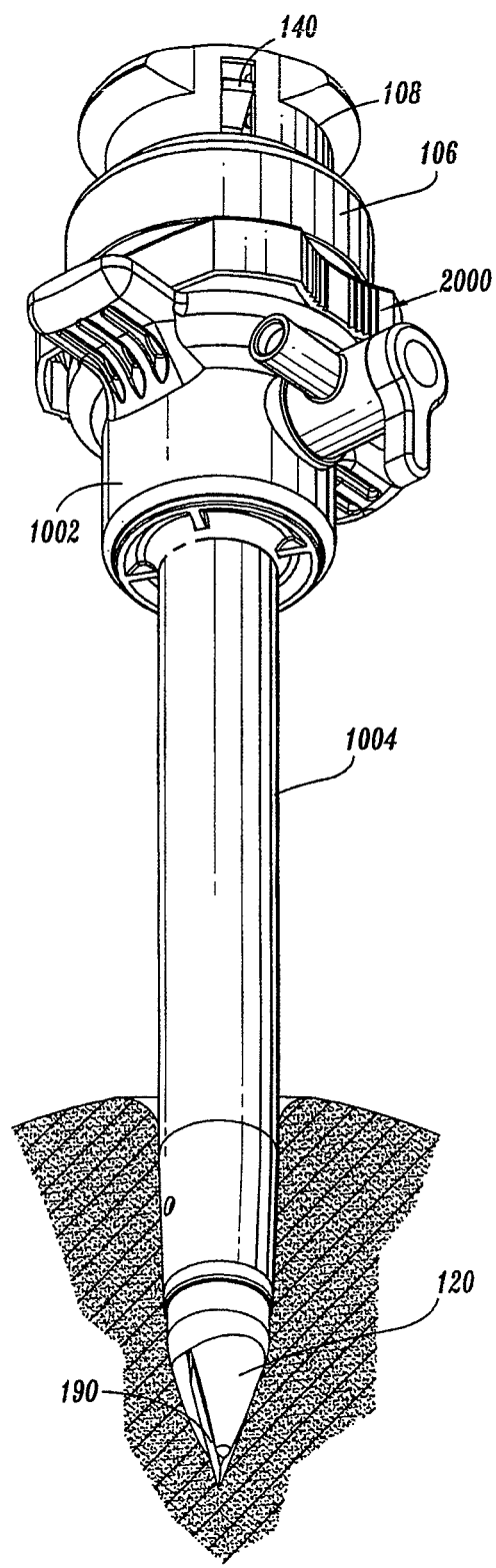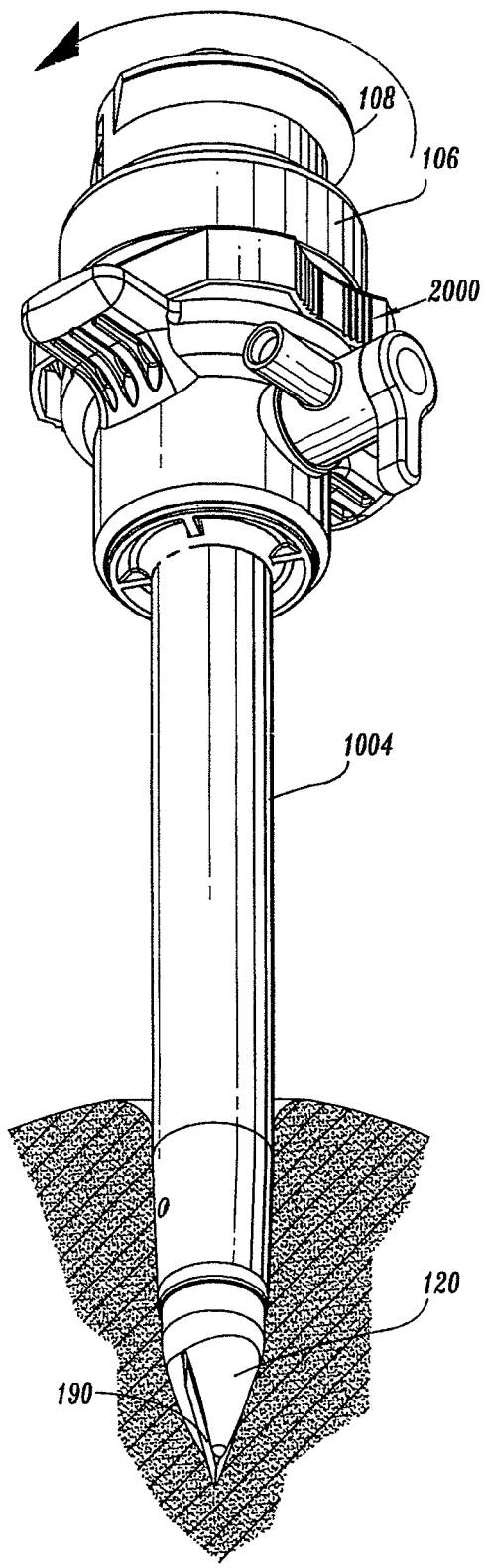
FIG. 18  FIG. 19

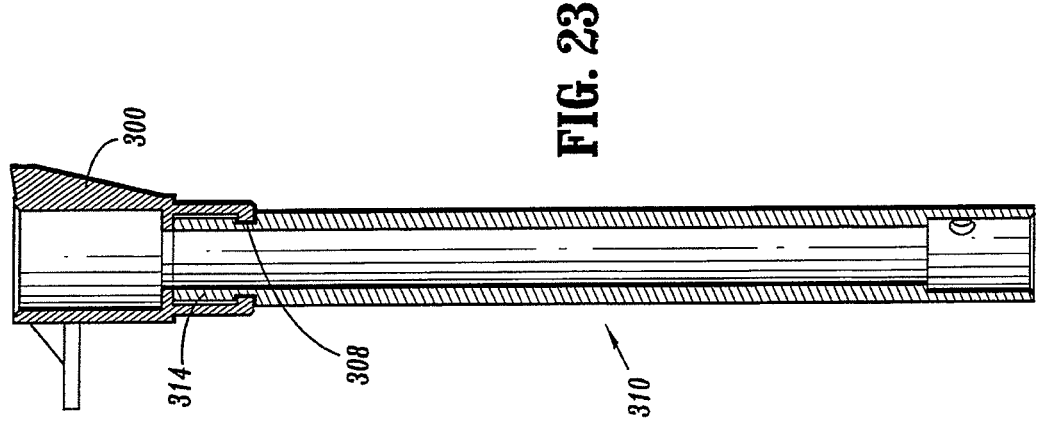
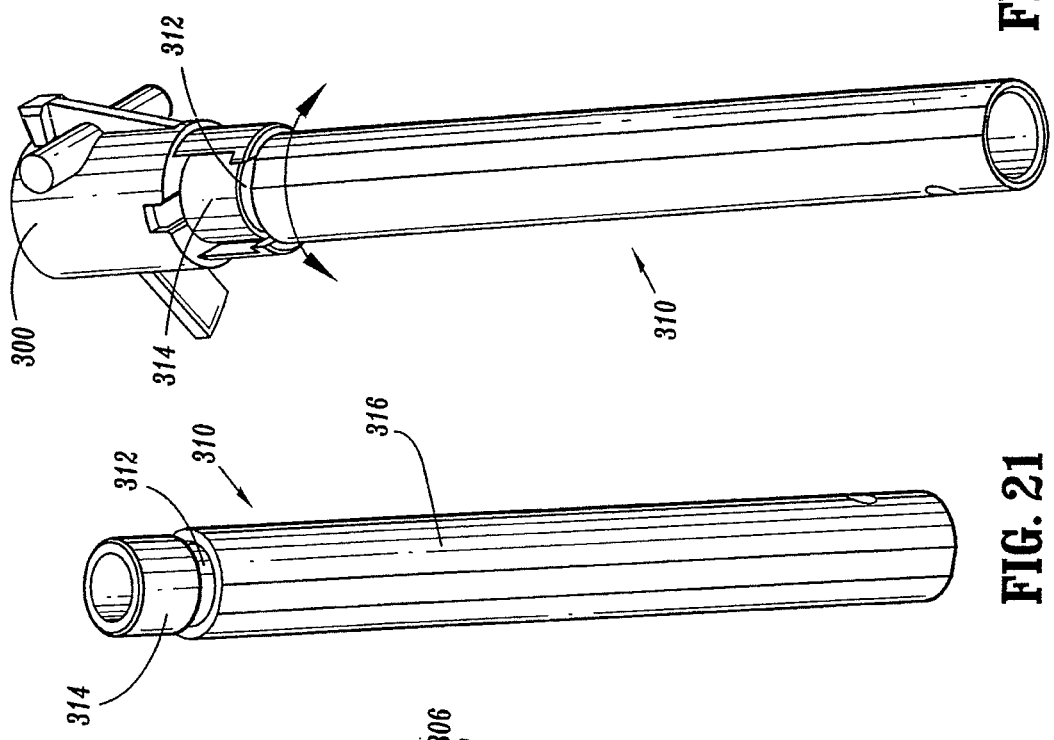
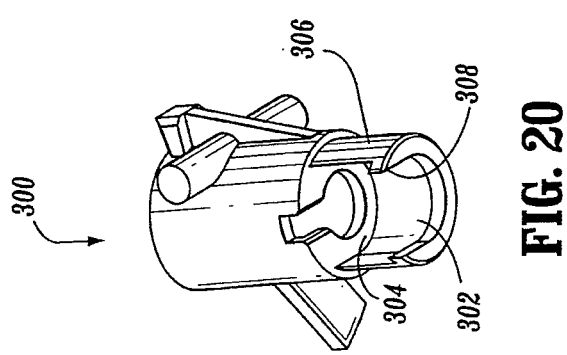
FIG. 20
FIG. 21
FIG. 22
FIG. 23

TROCAR ASSEMBLY WITH ROTATABLE OBTURATOR HOUSING

CROSS REFERENCE TO RELATED APPLICATIONS

This application is a Continuation of, and claims the benefit of and priority to U.S. patent application Ser. No. 11/171,052, filed Jun. 30, 2005 now U.S. Pat. No. 7,988,670, and incorporates its entire contents by reference herein.

BACKGROUND

1. Technical Field

The present disclosure relates to a trocar assembly for use in minimally invasive surgical procedures, such as endoscopic or laparoscopic type procedures.

2. Background of the Related Art

Minimally invasive procedures are continually increasing in number and variation. Forming a relatively small diameter temporary pathway to the surgical site is a key feature of most minimally invasive surgical procedures. The most common method of providing such a pathway is by inserting a trocar assembly through the skin. In many procedures, the trocar assembly is inserted into an insufflated body cavity of a patient. In such procedures, the trocar assemblies with seal mechanisms are utilized to provide the necessary pathway to the surgical site while minimizing leakage of insufflation gases.

Trocar assemblies typically include an obturator which is removably inserted through a cannula. The obturator may include a safety shield which protects against unintentional puncturing by the sharpened tip of the obturator. The safety shield includes a mechanism which controls the relative movement and locking of the safety shield. One example of a safety shield mechanism is disclosed in commonly assigned U.S. Pat. No. 6,319,266 to Stellon et al., the entire contents of which are hereby incorporated by reference.

Insertion of the trocar assembly through the body wall of the patient can require the application of significant axial force. Typically, during the procedure, the obturator housing is grasped and pressure is applied to the assembly. In addition to application of pressure, the surgeon may rotate the obturator housing, either intentionally or unintentionally, to pass the penetrating tip through the tissue. However, any torquing of the obturator housing may be undesirable, particularly, with an obturator having a flat bladed tip. As rotation of the flat bladed tip may cause undesired tearing of tissue.

Accordingly, there is a need for further improvement in trocar obturator assemblies including assemblies which reduce undesirable tearing of tissue.

SUMMARY

Accordingly, the present disclosure is directed to further improvements in trocar technology. In one preferred embodiment, the trocar system includes a cannula having a cannula housing and a cannula sleeve extending from the cannula housing, and an obturator at least partially positionable within the cannula. The obturator includes an obturator housing, an obturator shaft connected to the obturator housing, a generally flat obturator blade connected to the obturator shaft, a protective member coaxially mounted about the obturator blade and being adapted for longitudinal movement between a first position substantially enclosing the obturator blade and a second position to at least partially expose the obturator blade, and a latch member positioned in the obturator housing to prevent longitudinal movement of the protective member. The obturator shaft and the obturator blade are adapted for relative rotational movement. The latch member is moveable from an initial position securing the protective guard in the first position to an actuated position operatively releasing the protective guard to permit the protective guard to move to the second position thereof. The latch member is preferably adapted to move to the actuated position upon approximating the obturator housing and the cannula housing.

In one preferred embodiment, the obturator includes a blade mount connected to the obturator shaft with the blade mount and the obturator shaft being adapted for relative rotational movement about the longitudinal axis. The blade mount houses the obturator blade. The obturator shaft may be secured to the obturator housing whereby rotational movement of the obturator housing causes corresponding rotational movement of the obturator shaft.

An indicator member may be mounted adjacent the obturator housing and operatively connected to the protective member. The indicator member is movable upon movement of the protective guard to the second position to provide visual confirmation to the user of the positioning of the protective guard. The protective guard is normally biased toward the first position.

The obturator preferably includes a release member mounted to the obturator housing and operatively coupled with the latch member. The release member is adapted to move the latch member to the actuated position upon mating of the obturator housing and the cannula housing. The release member includes a release button positioned to engage the cannula housing upon mating of the obturator housing and the cannula housing to thereby displace the release member and cause movement of the latch member to the actuated position.

The obturator preferably includes an indicator collar disposed within the obturator housing and mounted to the protective member. The indicator collar is adapted for longitudinal movement with the protective member upon movement of the latch member to the actuated position. The indicator collar and the protective member are adapted for relative rotational movement. The indicator collar may include an indicator member adapted for providing visual confirmation to the user of the positioning of the protective guard.

The cannula assembly may include a seal assembly having a seal housing and an internal seal. The seal housing is mountable to the cannula housing.

In another preferred embodiment, an obturator assembly for penetrating tissue is provided. The obturator assembly includes an obturator housing, an obturator shaft connected to the obturator housing, a generally flat obturator blade connected to the obturator shaft with the obturator shaft and the obturator blade being adapted for relative rotational movement, a protective member mounted about the obturator blade and being adapted for longitudinal movement between a first position substantially enclosing the obturator blade and a second position to at least partially expose the obturator blade, and a latch member positioned in the obturator housing to prevent movement of the protective member. The latch member is moveable from an initial position securing the protective member in the first position to an actuated position operatively releasing the protective member to permit the protective member to move to the second position thereof. A release member may be mounted to the obturator housing and operatively coupled with the latch member. The release member has a release button positioned to engage the cannula assembly upon mating of the obturator housing and the cannula assembly to thereby displace the release member and cause movement of the latch member to the actuated position.

An indicator collar may be disposed within the obturator housing and mounted to the protective member. The indicator collar is adapted for longitudinal movement with the protective member upon movement of the latch member to the actuated position. The indicator collar and the protective member are adapted for relative rotational movement. The indicator collar includes an indicator member adapted for providing visual confirmation to the user of the positioning of the protective guard.

In another preferred embodiment, an obturator assembly includes an obturator housing, an obturator shaft connected to the obturator housing, a generally flat obturator blade connected to the obturator shaft with the obturator shaft and obturator blade being adapted for relative rotational movement, and a protective member mounted around the obturator blade. The protective member is adapted for longitudinal movement between a first position substantially enclosing the obturator blade and a second position to at least partially expose the obturator blade. The protective member may be rotatably attached to the obturator housing.

BRIEF DESCRIPTION OF THE DRAWINGS

Preferred embodiments of the present disclosure are described hereinbelow with references to the drawings, wherein:

FIG. 1 is a perspective view of an embodiment of a trocar assembly constructed in accordance with the present disclosure;

FIG. 2 is a perspective view with parts separated of the trocar assembly illustrating the cannula assembly and the obturator assembly in accordance with the embodiment of FIG. 1;

FIGS. 11-12 are perspective views illustrating the components of the latch mechanism in accordance with the embodiment of FIGS. 1-10;

FIG. 13 is a perspective view of the obturator shaft and the obturator blade in accordance with the embodiment of FIGS. 1-12;

FIG. 14 is a side cross-sectional view of the trocar assembly illustrating the obturator assembly mounted relative to the cannula assembly and the latch member in an actuated position in accordance with the embodiment of FIGS. 1-13;

FIG. 15 is an enlarged side cross-sectional view illustrating the relationship of the components of the latch member in an actuated position in accordance with the embodiment of FIGS. 1-14;

FIG. 18 is a perspective view illustrating insertion of the trocar assembly within tissue;

FIG. 19 is a view similar to the view of FIG. 18 illustrating rotation of the obturator housing of the obturator assembly;

FIG. 20 is a perspective view of an alternative embodiment of an indicator collar for use with the obturator assembly;

FIG. 21 is a perspective view of a shield member for use with the indicator collar in accordance with the embodiment of FIG. 20;

FIG. 22 is a perspective view illustrating mounting of the indicator collar to the shield member in accordance with the embodiment of FIGS. 20-21; and FIG. 23 is a side cross-sectional view of the assembled indicator collar and shield member in accordance with the embodiment of FIGS. 20-22.

DETAIL DESCRIPTION OF PREFERRED EMBODIMENTS

Figure 3:
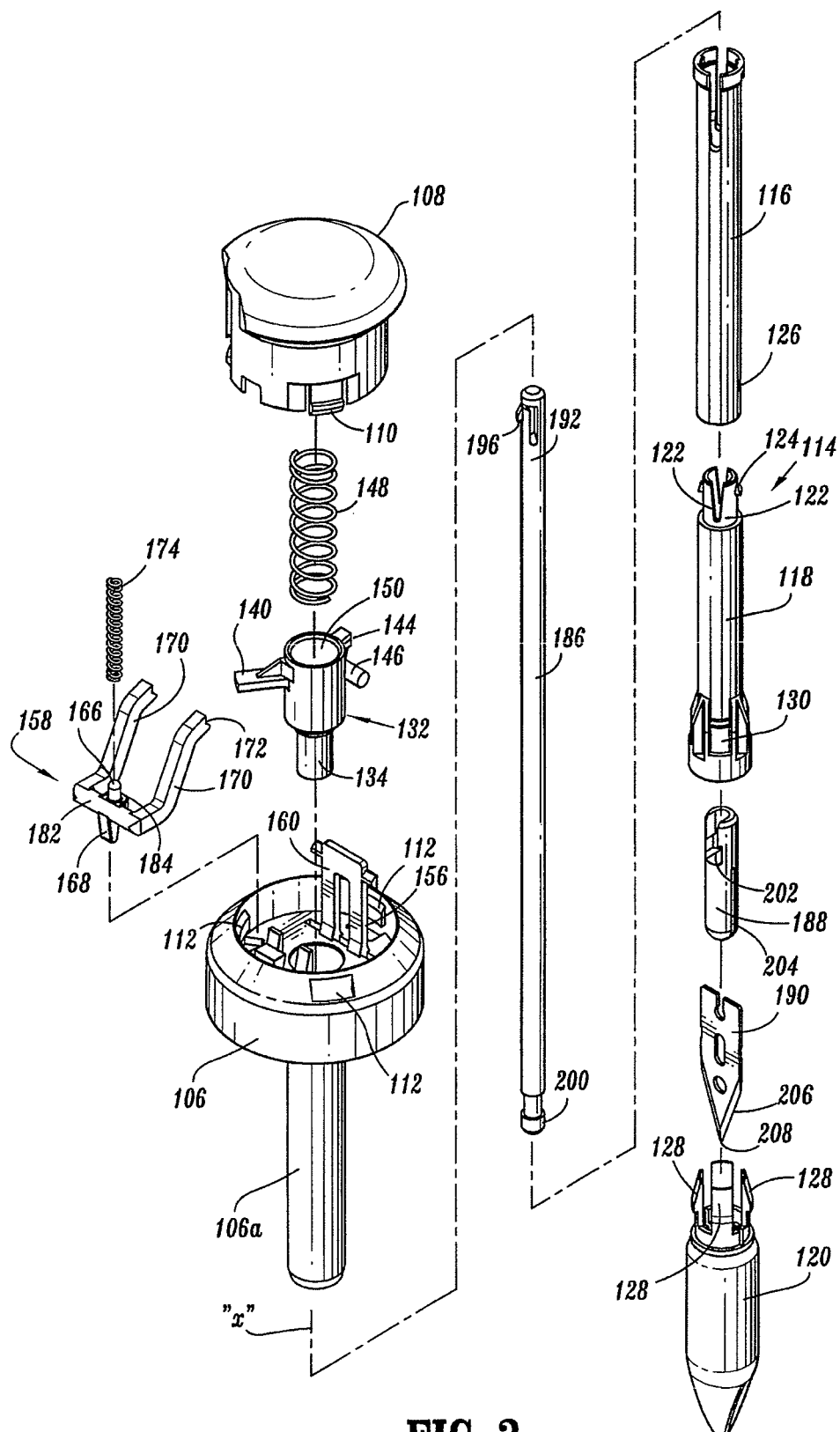
FIG. 3 is a perspective view with parts separated of the obturator assembly in accordance with the embodiment of FIGS. 1-2.

Referring now in detail to the drawing figures, in which, like references numerals identify similar or identical elements, there is illustrated, in FIGS. 1 and 2, a trocar assembly constructed in accordance with a preferred embodiment of the present disclosure and designated generally by reference numeral 10. Trocar assembly 10 is particularly adapted for use in minimally invasive surgical procedures such as endoscopic or laparoscopic procedures. Generally, trocar assembly 10 includes two principal subassemblies, namely, obturator assembly 100 and cannula assembly 1000.

Cannula assembly 1000 may be any cannula assembly suitable for use in a laparoscopic surgical procedure. In one preferred embodiment, cannula assembly 1000 includes cannula housing 1002 and cannula sleeve 1004 extending from the cannula housing 1002. Either or both cannula housing 1002 and cannula sleeve 1004 may be transparent in part or in whole and are fabricated from biocompatible metal or polymeric material. Cannula assembly 1000 may include an internal seal such as a duck-bill valve or other zero closure valve adapted to close in the absence of a surgical instrument to prevent passage of insufflation gases through the cannula assembly 1000.

Trocar assembly 10 may also include a seal assembly 2000 which is preferably releasably mounted to cannula housing 1002. Means for releasably connected seal assembly 2000 to cannula housing 1002 may include a bayonet coupling, threaded connection, latch, friction fit, tongue and groove arrangements, snap-fit, etc. Seal assembly 2000 includes seal housing 2002 and at least one internal seal which is adapted to form a fluid tight seal about an instrument inserted through the seal assembly 2000. One suitable seal may be the fabric seal disclosed in commonly assigned U.S. patent application Ser. No. 10/165,133, filed Jun. 6, 2002, the entire contents of which are incorporated herein by reference. The seal disclosed in the '133 application may be a flat septum seal having a first layer of resilient material and a second fabric layer juxtaposed relative to the first layer. Further details of the seal may be ascertained by reference to the '133 application. Seal assembly 2000 may or may not be a component of cannula assembly 1000. For example, the seal assembly may be a separate, removable assembly. In the alternative, the seal assembly may comprise an integral part of the cannula assembly 1000 and not be removable.

Figures 4, 5:
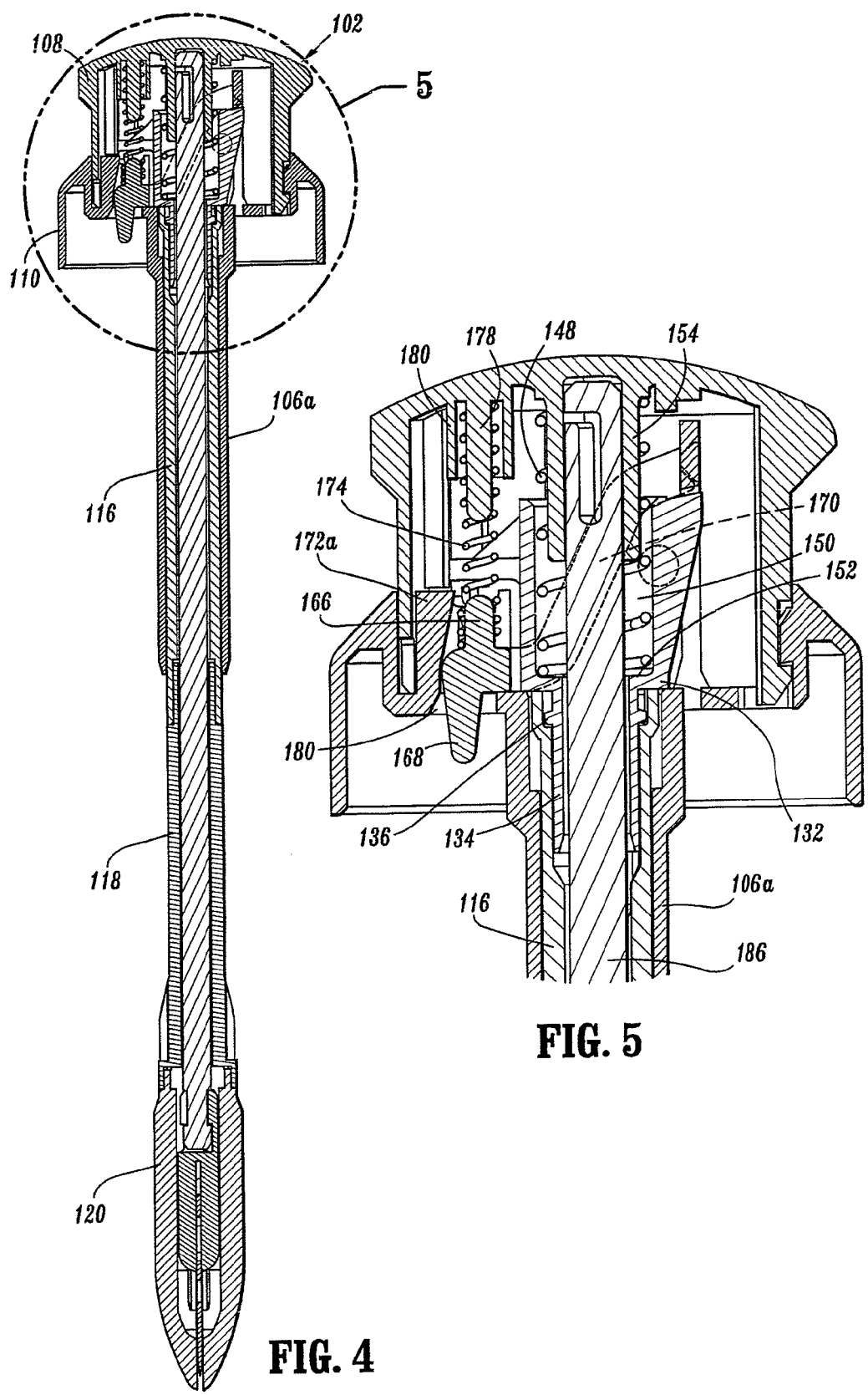
FIG. 4 is a side cross-sectional view of the obturator assembly in accordance with the embodiment of FIGS. 1-3.
FIG. 5 is an enlarged cross-sectional view of the indicated area of detail of FIG. 4 in accordance with the embodiment of FIGS. 1-4.

With reference now to FIGS. 3-4, in conjunction with FIG. 2, obturator assembly 100 includes obturator housing 102 and obturator shaft 104 extending distally from the housing 102. Obturator shaft 104 defines obturator axis "x" and will be discussed in greater detail hereinbelow. Obturator housing 102 includes housing base 106 and housing cover 108. Once the appropriate components are positioned therewithin (as described below), housing base 106 may be attached to housing cover 108 by engaging mating surfaces, for example, by resilient latches 110 of cover 108 interlocking with correspondingly dimensioned latch openings 112 of housing base 106. Preferably, to uniformly connect base 106 and cover 108 at least three corresponding latches 110 and openings 112 are spaced evenly around the circumference of the cover 108 and the base 108, respectively. Preferably, obturator housing 102 is configured and dimensioned to functionally cooperate with cannula that range in size, e.g., from about 5 mm to about 15 mm in diameter.

Obturator assembly 100 includes protective shield 114. Protective shield 114 includes shield member 116, shield extension 118 and blade guard 120 operatively connected to each other to define an outer member of obturator assembly 100. In one preferred embodiment, shield member 116 is connected to shield extension 118 through an arrangement including diametrical tabs 122 extending from the shield extension 118, which are received within the internal lumen of shield member 116 in frictional relation therewith, or a snap-fit. Diametrical tabs 122 may further include circular or cylindrical bases 124 which are received within corresponding openings 126 of shield member 116 in snap relation therewith. Similarly, blade guard 120 includes a plurality, e.g., four, of axially depending tabs 128 which are received within correspondingly dimensioned tab openings 130 of shield extension 118 to connect the two components. Other means for connecting the components of protective shield 114 are also envisioned including snap fit arrangements, adhesives, welding tongue and groove arrangements, etc. In other embodiments, protective shield 114 is single component. In the assembled condition, shield member 116 of protective shield 114 extends within housing base 106, particularly, cylindrical portion 106*a* of the housing base 106. Protective shield 114 is adapted for axial movement along axis "x" and relative to obturator housing 102 as will be discussed in greater detail hereinbelow.

Figure 6:
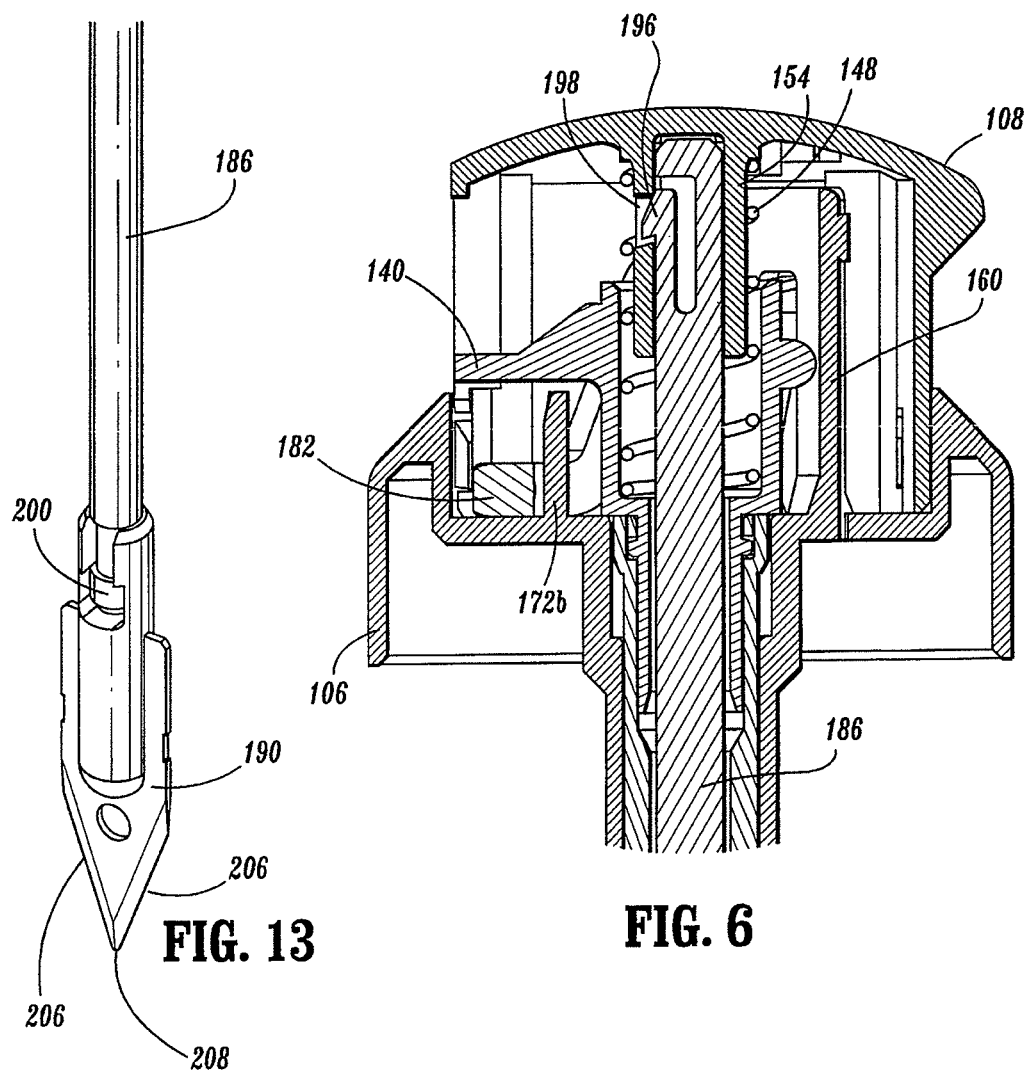
FIG. 6 is a second enlarged cross-sectional view of the obturator housing of the obturator assembly in accordance with the embodiment of FIGS. 1-5.
Figure 7:
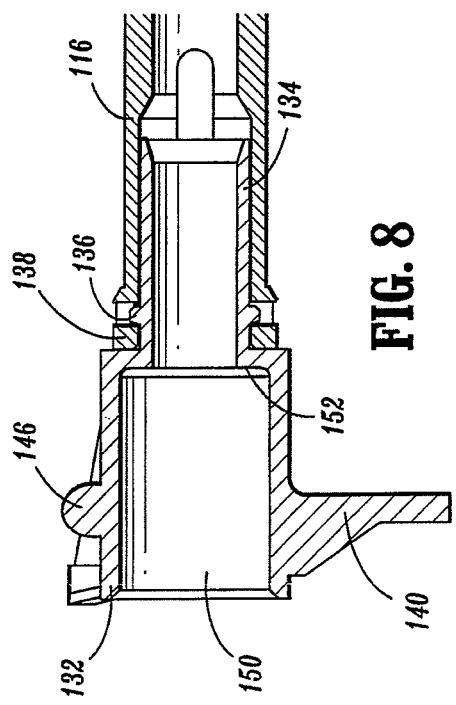
FIG. 7 is a perspective view of the indicator collar of the obturator housing mounted to the shield member in accordance with the embodiment of FIGS. 1-6.
Figure 8:
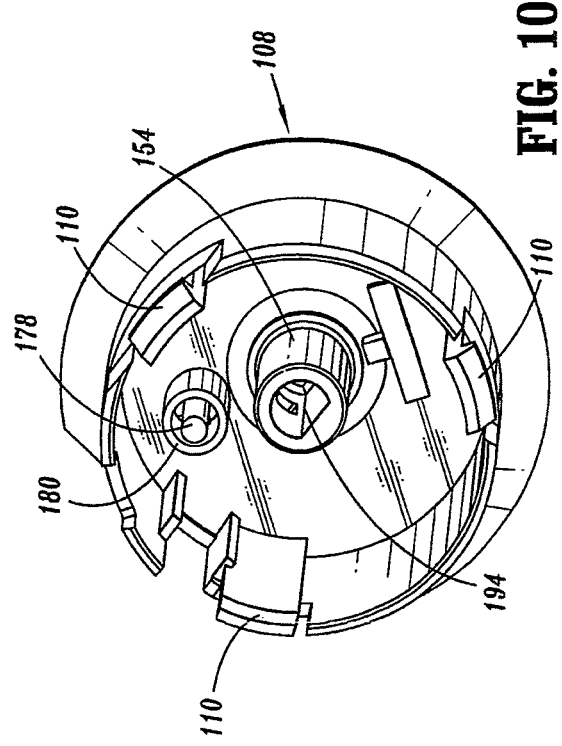
FIG. 8 is a side cross-sectional view of the indicator collar and shield member in accordance with the embodiment of FIGS. 1-7.
Figure 9:
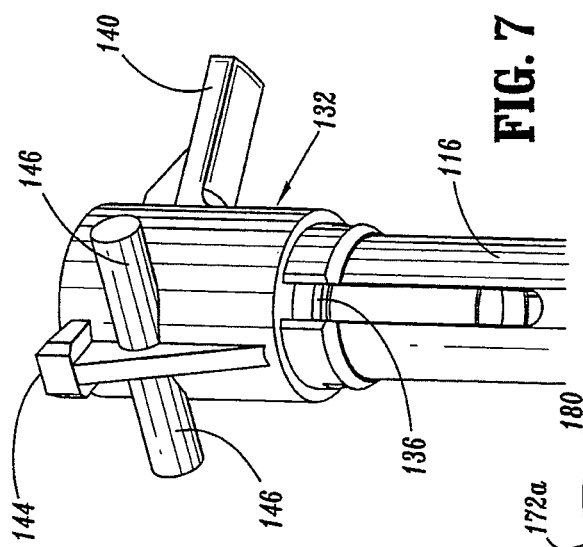
FIG. 9 is a perspective view of the housing base of the obturator housing in accordance with the embodiment of FIGS. 1-8.

Referring now to FIGS. 3-8, obturator assembly 100 further includes indicator collar 132 which is secured within the proximal end of shield member 116. In one preferred arrangement, indicator collar 132 defines distal collar extension 134. Collar extension 134 includes annular rim 136 on its outer surface. Annular rim 136 is contained within shield member 116 through its engagement with radial tabs 138 of shield member 116 as best shown in FIGS. 7 and 8. With this arrangement, indicator collar 132 is adapted to rotate relative to shield member 116—which will be discussed in greater detail hereinbelow.

Indicator collar 132 further includes a shield position indicator, such as indicator flag 140, extending transversely relative to the indicator collar 132. Indicator flag 140 is visible from the exterior of obturator housing 102 as it extends through groove 108*a* of housing cover 108 (see also FIGS. 2 and 7). Preferably, indicator flag 140 is colored to contrast sharply with the surrounding housing components. For example, indicator flag 140 may be red if the surrounding housing components are white or light colored. Indicator collar 132 further includes collar ledge 144 and a pair of posts 146 formed below the ledge 144 and extending radially outwardly from the ledge 144. Collar ledge 144 serves to releasably lock protective shield 114 in a distal position with respect to blade 190.

Figure 10:
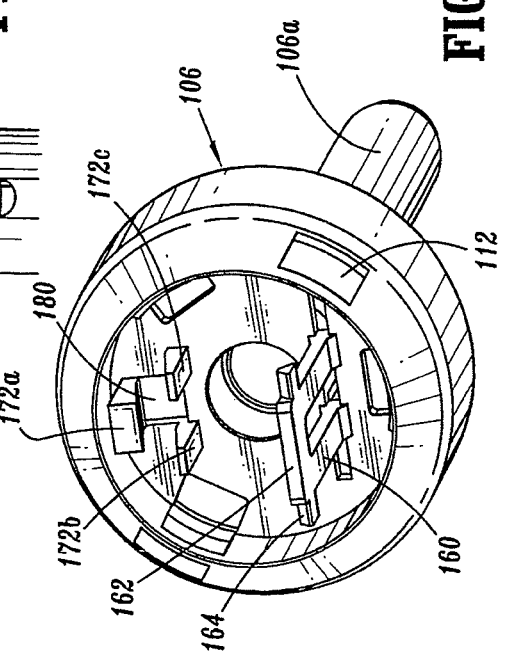
FIG. 10 is a perspective view of the housing cover of the obturator housing in accordance with the embodiment of FIGS. 1-9.

Indicator flag 140 and protective shield 114 are spring biased in the distal direction by coil spring 148. In particular, coil spring 148 is received within internal bore 150 of indicator collar 132 and engages internal shelf 152 (see FIG. 8) of the indicator collar 132. The proximal end of coil spring 138 is coaxially mounted about spring mount 154 (see FIG. 10) depending from the interior surface of housing cover 108.

Referring now to FIGS. 9-12, in conjunction with FIGS. 3-5, obturator assembly 100 includes a latching mechanism disposed within obturator housing 102 to prevent proximal movement of protective shield 114 until such time as the obturator assembly 100 is mounted to cannula assembly 1000 and the surgeon is prepared to begin trocar entry. Latching mechanism includes latch member 156, and release member such as slider 158, as best seen n FIG. 3. Latch member 156 has two vertical legs 160 connected by web 162. A pair of biasing posts 164 extends outwardly, one for each side of latch member 156. Collar ledge 144 of indicator collar 132 is engaged and secured by web 162 of latch member 156 when in an initial position of the latch member 156 as depicted in FIGS. 11-12. In the initial position of latch member 156, protective shield 114 is retained in a first extended position shown in FIG. 4. Latch member 156 is preferably molded as part of housing base 106 in cantilever fashion. However, latch member 156 may be formed as a separate element and secured to base 106 by suitable known techniques.

Slider 158 includes post 166 disposed at its lower end, arming button 168 extending distally from the distal face of slider 158 and a pair of slider legs 170 which terminate in crooks 172. Crooks 172 defined in slider legs 170 are configured and dimensioned to engage posts 164 of latch member 156, as shown in FIGS. 11 and 12. Slider 158 is distally biased by slider spring 174 which is maintained in axial alignment by slider post 166 of slider 158. The proximal end of slider spring 174 bears against the inner surface of housing cover 108 and is maintained in position between proximal post 178 and cylindrical base 180 formed in base 106, (see FIGS. 9 and 10). The distal biasing of slider 158 causes arming button 168 to project through opening 180 formed in housing base 106. The lower end or transverse leg 182 of slider 158 resides with mounting posts 172 *a-c* of housing base 106 with post base 184 of slider 158 residing within mounting posts 172*b*, 172*c*. (See FIG. 9). Mounting of obturator assembly 100 relative to cannula assembly 112 causes slider 158 to translate or rotate generally vertically in a generally proximal direction as will be described further hereinbelow.

With reference to FIGS. 4-6, in conjunction with FIG. 3, the components of obturator shaft 104 will be discussed. Obturator shaft 104 includes obturator rod 186, blade mount 188 and blade 190. Obturator rod 186 defines proximal end 192 having a general semi-circular cross-section and being received within correspondingly dimensioned opening 194 of spring mount 154 of housing cover 108 (see FIG. 10). The proximal end 192 further defines latch 196 which is received within side opening 198 of spring mount 154 in snap relation therewith to secure the two components (see FIG. 6).

With reference now to FIG. 13, in conjunction with FIG. 3, the distal end of obturator rod 186 defines collar 200. Blade mount 188 includes mounting recess 202 which is dimensioned to receive collar 200 of obturator rod 186. Mounting recess 202 is dimensioned to permit rotation of collar 200 and obturator rod 186 relative to blade mount 188. Blade mount 188 further includes knife slot 204 which accommodates knife blade 190. Knife blade 190 may be secured within knife slot 204 by conventional means including adhesives, cements, etc. Knife blade 196 is preferably a flat or thin blade and fabricated from stainless steel by a suitable process, e.g., by stamping or metal injection molding and includes opposed cutting edges 206 which extend to penetrating tip 208.

With reference now to FIGS. 14-15, a method of use and operation of trocar assembly 10 will be discussed. Obturator assembly 100 is inserted within cannula assembly 1000 and advanced to where obturator housing 102 is approximated with seal housing 2002 of the seal assembly 2000. Seal assembly 2000 may comprise a separate part or may be a component of cannula assembly 1000. Seal housing 2002 and housing base 106 of obturator housing 102 may be appropriately dimensioned to form a friction fit or may be coupled to each other by conventional means including bayonet coupling, tongue-groove, etc. Approximating the obturator housing 102 and the seal housing 202 releases the blade guard 120 from a locked condition, actuating the trocar assembly. With the obturator housing 102 and seal housing 2002 approximated, arming button 168 of slider 158 engages surface 2004 of seal housing 2002 and is forced upwardly (depicted by directional arrow "u") from the position depicted in FIG. 5 to the position depicted in FIGS. 14-15. During this movement, slider 158 pivots or angulates whereby legs 170 of slider 158 push latch member 156 in a radial outward direction (depicted by directional arrow "z") such that web portion 162 of latch member 156 is out of axial alignment with ledge 144 of indicator collar 132. In this position, indicator collar 132 and protective shield 114 are free to axially move.

Figures 16, 17:
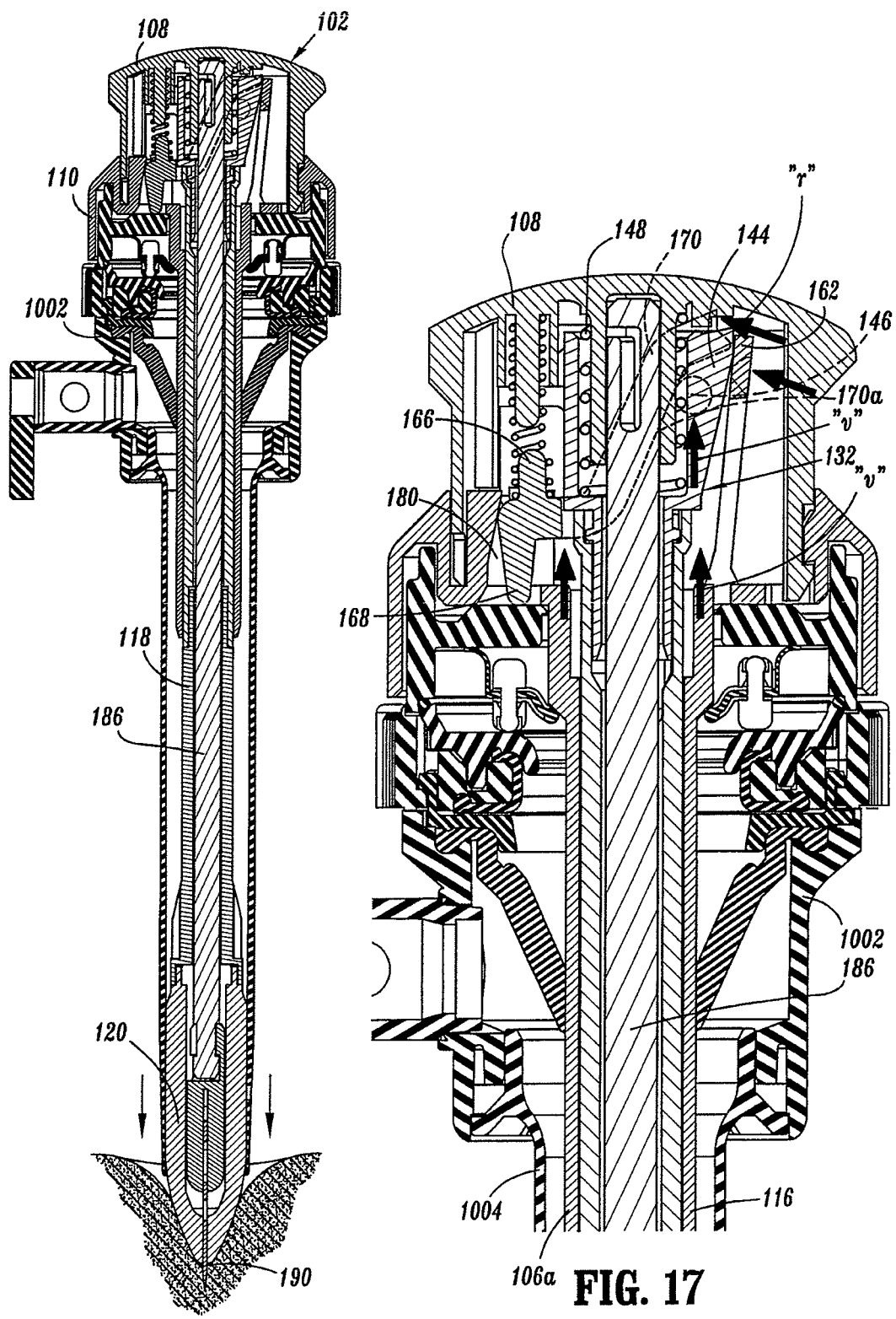
FIG. 16 is a view similar to the view of FIG. 14 illustrating the protective shield of the obturator assembly in a retracted position in accordance with the embodiment of FIGS. 1-15.
FIG. 17 is a view similar to the view of FIG. 15 illustrating the relationship of the components of the latch member when the protective shield is in the retracted position in accordance with the embodiment of FIGS. 1-16.

Referring now to FIGS. 16-17, the surgeon begins to insert trocar assembly 10 through the body wall of the patient. Blade guard 120 contacts the tissue and is driven upwardly to cause protective shield 114 and indicator collar 132 to move proximally (depicted by directional arrow "v") against the bias of coil spring 148. Such movement exposes obturator blade 190 to incise the tissue. This armed condition of obturator assembly 100 is visually verified by the proximal location of indicator flag 140 of indicator collar 132. In addition, proximal movement of indicator collar 132 causes posts 146 of the indicator collar 132 to ride along outer surfaces 170a of legs 170 of slider 158 to thereby move the slider 158 at least radially inwardly and upwardly (as shown by the directional arrows "r") in a general aligned position relative to the obturator axis "x". FIG. 17 illustrates this actuated position of latch member 156. With obturator blade 190 exposed, the surgeon may apply a distally-directed force to obturator assembly 100 to cause penetration through the tissue. The surgeon may rotate obturator housing 102 during manipulation and advancement of obturator assembly 100 into the tissue without concern of obturator blade 190 rotating. In particular, the rotatable coupling of obturator rod 186 with knife mount 188 allows the knife blade 190 to remain stationary within the tissue even in the surgeon rotates obturator housing 102. In addition, upon rotation of obturator housing 102, protective shield 114 including shield member 116, shield extension 118 and blade guard 120 also remain stationary due to the rotatable coupling of shield member 116 with indicator collar 132. This is desirable in that any rotational movement of knife blade 190 may cause unnecessary damage to the tissue of the patient. FIGS. 18-19 illustrate rotation of obturator housing 102 while blade guard 120 and knife blade 190 remain stationary during advancement of trocar assembly 10 within tissue "t". It is noted that indicator flag 140 in its proximal position provides visual confirmation of the armed condition of knife blade 190.

Once knife blade 190 and blade guard 120 pass through the body wall of the patient protective shield 114 moves distally to cover blade 190 and ledge 144 of indicator collar 132 moves into engagement with web portion 162 of latch member 156. In particular, indicator collar 132 and protective shield 116 are driven distally under the influence of coil spring 148. Concurrently with this movement, slider 158, which is aligned relative to axis "x", is driven distally under the influence of coil spring 174. In the respective positions of indicator collar 132 and slider 158 depicted in FIGS. 4 and 5, collar ledge 144 of indicator collar 132 securely engages web 162 of latch member 156 to secure protective shield 114 in its extended position. The obturator assembly 100 is removed from cannula assembly 1000 and surgery is performed with instruments inserted through cannula assembly 1000.

With reference to FIGS. 20-23, alternative embodiments of indicator collar and shield member are illustrated. This embodiment is adapted to also permit relative rotation of these two components. Indicator collar 300 includes internal bore 302 and recess 304 extending through side wall 306 of the collar 300. Indicator collar 300 further defines internal annular tab 308 extending inwardly within bore 302. Shield member 310 defines annular peripheral slot or neck 312 having a reduced cross-section relative to the cross-sections of adjacent shield sections 314, 316. In the assembled condition of the components, peripheral slot 312 receives annular tab 308 of indicator collar 300 with shield section or head 314 within bore 302 of the collar 300. Peripheral slot 312 and annular tab 308 are appropriately dimensioned to permit rotation of the components. In other respects, indicator collar 300 and shield member 310 operate in a similar manner to their counterpart components in the embodiment of FIGS. 1-19.

Except where noted otherwise, the materials utilized in the components of the presently disclosed trocar assembly generally include materials such as, for example, ABS, polycarbonate, stainless steel, titanium and any other suitable biocompatible metals and/or polymeric materials. A preferred ABS material is CYCOLAC which is available from General Electric. A preferred polycarbonate material is also available from General Electric under the trademark LEXAN. An alternative polycarbonate material which may be utilized is CALIBRE polycarbonate available from Dow Chemical Company. The polycarbonate materials may be partially glass filled for added strength.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:
1. A surgical penetrating system, which comprises:
a housing;
a shaft connected to the housing and defining a longitudinal axis;
a blade coupled to the shaft such that the blade is rotatable relative to the shaft about the longitudinal axis, the blade being generally flat; and
a protective member coaxially mounted about the blade and being at least partially positioned within the housing and rotatable relative to the housing, the protective member adapted for longitudinal movement between a first position substantially enclosing the blade and a second position to at least partially expose the blade.

2. The surgical penetrating system of claim 1 including a blade mount connected to the shaft, the blade mount and the shaft adapted for relative rotational movement about the longitudinal axis, the blade mount housing at least a portion of the blade.

3. The surgical penetrating system of claim 1 wherein the shaft is secured to the housing whereby rotational movement of the housing causes corresponding rotational movement of the shaft.

4. The surgical penetrating system of claim 1 wherein the protective member is normally biased toward the first position.

5. The surgical penetrating system of claim 1 including a cannula having a cannula housing and a cannula sleeve extending from the cannula housing, the shaft being at least partially positioned within the cannula sleeve.

6. The surgical penetrating system of claim 1 wherein the housing is adapted for rotational movement relative to the blade.

7. The surgical penetrating system of claim 1 including a latch member positioned in the housing to prevent longitudinal movement of the protective member.

8. The surgical penetrating system of claim 7 wherein the latch member has an initial position securing the protective member in the first position.

9. The surgical penetrating system of claim 8 wherein the latch member is movable to an actuated position operatively releasing the protective member to permit the protective member to move to the second position.

10. The surgical penetrating system of claim 9 including a release member mounted to the housing and operatively coupled with the latch member, the release member adapted to move the latch member to the actuated position.

11. The surgical penetrating system of claim 10 wherein the release member includes a release button configured to displace the release member and cause movement of the latch member to the actuated position.

12. The surgical penetrating system of claim 9 including an indicator collar disposed within the housing and mounted to the protective member, the indicator collar being adapted for longitudinal movement with the protective member upon movement of the latch member to the actuated position.

13. The surgical penetrating system of claim 12 wherein the indicator collar and the protective member are adapted for relative rotational movement.

14. The surgical penetrating system of claim 12 wherein the indicator collar includes an indicator member adapted for providing visual confirmation to the user of the positioning of the protective member.

15. A surgical penetrating system, which comprises:
a housing;
a shaft connected to the housing and defining a longitudinal axis;
a blade coupled to the shaft such that the blade is rotatable with respect to the shaft about the longitudinal axis, the blade being generally flat; and
a protective member coaxially mounted about the blade and having a shield and a blade guard connected to the shield, the shaft being at least partially positioned within the shield and the blade being at least partially positioned within the blade guard, the protective member being adapted for longitudinal movement between a first position substantially enclosing the blade and a second position to at least partially expose the blade, the housing adapted for rotational movement relative to the protective member and to the blade.

16. The surgical penetrating system of claim 15 including a latch member positioned in the housing to prevent longitudinal movement of the protective member.

17. The surgical penetrating system of claim 15 including a blade mount dimensioned to rotatably connect the blade and the shaft.

18. The surgical penetrating system of claim 17 wherein one of the blade mount and the shaft includes a collar, and the other of the blade mount and the shaft includes a mounting recess for receiving the collar, the collar dimensioned to rotate within the mounting recess to permit rotational movement of the blade relative to the shaft.

19. A surgical penetrating system, which comprises:
a housing;
a shaft connected to the housing and defining a longitudinal axis;
a blade coupled to the shaft such that the blade is rotatable relative to the shaft about the longitudinal axis, the blade being generally flat; and
a protective member coaxially mounted about the blade and having a shield and a blade guard connected to the shield, the shaft being at least partially positioned within the shield and the blade being at least partially positioned within the blade guard, the protective member being adapted for longitudinal movement between a first position substantially enclosing the blade and a second position to at least partially expose the blade.

20. A surgical penetrating system, which comprises:
a housing;
a shaft connected to the housing and defining a longitudinal axis;
a blade mount connected to the shaft, the blade mount and the shaft adapted for relative rotational movement about the longitudinal axis;
a blade at least partially housed within the blade mount, the blade being rotatable with the blade mount and relative to the shaft about the longitudinal axis, the blade being generally flat;
a protective member coaxially mounted about the blade and being adapted for longitudinal movement between a first position substantially enclosing the blade and a second position to at least partially expose the blade; and
one of the blade mount and the shaft including a collar, and the other of the blade mount and the shaft including a mounting recess for receiving the collar, the collar dimensioned to rotate within the mounting recess to permit rotational movement of the blade relative to the shaft.

* * * * *